US010598638B2

(12) United States Patent
Olovsson et al.

(10) Patent No.: US 10,598,638 B2
(45) Date of Patent: Mar. 24, 2020

(54) CHROMATOGRAPHY LAB SYSTEM INCLUDING COOLING COMPARTMENT AND IDENTIFYING DEVICE

(71) Applicant: GE Healthcare Bio-Sciences AB, Uppsala (SE)

(72) Inventors: Bjorn Olovsson, Uppsala (SE); Karol Lacki, Uppsala (SE); Mikael Berg, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 16/175,784

(22) Filed: Oct. 30, 2018

(65) Prior Publication Data

US 2019/0128859 A1 May 2, 2019

Related U.S. Application Data

(63) Continuation of application No. 15/309,739, filed as application No. PCT/EP2015/059793 on May 5, 2015, now Pat. No. 10,113,996.

(30) Foreign Application Priority Data

May 14, 2014 (SE) ...................................... 1450561

(51) Int. Cl.
*G01N 30/82* (2006.01)
*G01N 35/00* (2006.01)

(52) U.S. Cl.
CPC ....... *G01N 30/82* (2013.01); *G01N 35/00732* (2013.01); *G01N 2035/00435* (2013.01);
(Continued)

(58) Field of Classification Search
CPC ............... G01N 35/1097; G01N 30/38; G01N 2030/8804; G01N 2035/00326;
(Continued)

(56) References Cited

U.S. PATENT DOCUMENTS 3,185,211 A 5/1965 Crawford, Jr. et al.
5,228,988 A * 7/1993 Sanford ................ G01N 30/32 210/198.2

(Continued)

FOREIGN PATENT DOCUMENTS

CN 101795769 8/2010
CN 201561961 8/2010

(Continued)

OTHER PUBLICATIONS

English Translation of CN Office Action and Search Report for Chinese Patent Appl. No. 201580024870.5, dated Sep. 13, 2017, 18 pages.

(Continued)

*Primary Examiner* — Brandi N Hopkins
(74) *Attorney, Agent, or Firm* — Eversheds Sutherland (US) LLP

(57) ABSTRACT

A chromatography lab system comprising a cooling compartment arranged to hold both fraction collector devices and sample containers, whereby the cooling compartment comprises an identifying device which is arranged to identify the fraction collector devices such that fractions from the chromatography are collected only in the fraction collector devices.

10 Claims, 3 Drawing Sheets

(52) U.S. Cl.
CPC .............. *G01N 2035/00792* (2013.01); *G01N 2035/00851* (2013.01)

(58) Field of Classification Search
CPC .. G01N 30/24; G01N 30/88; G01N 2030/027; G01N 2030/8881; G01N 35/1011; G01N 30/82; B01D 29/60; B01D 15/08; B01D 2201/54; B01D 15/10; B01D 17/12; Y10T 137/6525; Y10T 137/85986; Y10T 137/6416; Y10T 137/6851; Y10T 137/87885; Y10T 436/2575; B01L 3/0234; B01L 9/06; B01L 2200/0605; B01L 2300/021; B01L 2200/025; B01L 2200/143; B01L 2300/0829
See application file for complete search history.

(56) References Cited

U.S. PATENT DOCUMENTS

| | | | | |
|---|---|---|---|---|
| 5,277,871 | A | 1/1994 | Fujii et al. | |
| 5,301,261 | A | 4/1994 | Poole et al. | |
| 5,601,707 | A * | 2/1997 | Clay | B01D 11/0203 210/198.2 |
| 7,374,674 | B2 | 5/2008 | Miyauchi et al. | |
| 9,086,422 | B2 | 7/2015 | Bystron et al. | |
| 9,566,537 | B2 | 2/2017 | Geng | |
| 10,113,996 | B2 | 10/2018 | Olovsson et al. | |
| 2004/0238427 | A1 | 12/2004 | Shuzo et al. | |
| 2007/0116611 | A1* | 5/2007 | DeMarco | G01N 30/82 422/400 |
| 2008/0164210 | A1 | 7/2008 | DeMarco | |
| 2011/0036450 | A1* | 2/2011 | Carlsson | B01L 3/0234 141/1 |
| 2013/0288355 | A1 | 10/2013 | DeWitte et al. | |

FOREIGN PATENT DOCUMENTS

| | | |
|---|---|---|
| CN | 102103146 | 6/2011 |
| CN | 103063753 | 4/2013 |
| EP | 2891881 | 7/2015 |
| JP | 2001242149 | 9/2001 |
| JP | 2005106813 A | 4/2005 |
| JP | 2012511725 A | 5/2012 |
| JP | 2015534635 A | 12/2015 |
| WO | 2012096649 | 7/2012 |
| WO | 2014032285 | 3/2014 |

OTHER PUBLICATIONS

International Search Report and Written Opinion regarding International Application No. PCT/EP2015/059793, dated Aug. 18, 2015, 10 pages.

International-Type Search Report regarding SE Application No. 1450561-4, dated Dec. 9, 2014, 6 pages.

Japan Notice of Preliminary Rejection for Japanese Patent Application No. 2016-567398, dated Feb. 26, 2019, 4 pages.

* cited by examiner

CHROMATOGRAPHY LAB SYSTEM INCLUDING COOLING COMPARTMENT AND IDENTIFYING DEVICE

FIELD OF THE INVENTION

The present invention relates to a chromatography lab system comprising a cooling compartment and to a method in a chromatography lab system.

BACKGROUND

In chromatography lab systems the samples that are fed to the chromatography column are often positioned outside the system. In some applications the sample needs to be cooled.

This is sometimes solved by for example using external refrigerators or ice baths for the sample. This adds complexity to the chromatography lab system.

SUMMARY OF THE INVENTION

One object of the invention is to provide a convenient and compact chromatography lab system.

Another object of the invention is to provide a functional method for cooling sample in a chromatography lab system.

This is achieved in a chromatography lab system comprising a cooling compartment arranged to hold both fraction collector devices and sample containers, whereby the cooling compartment comprises an identifying device which is arranged to identify the fraction collector devices such that fractions from the chromatography are collected only in the fraction collector devices.

This is also achieved in a method for cooling samples in a chromatography lab system comprising the steps of:

- placing a sample container in the same cooling compartment as fraction collector devices are stored in, and
- identifying the fraction collector devices such that fractions are collected only in the fraction collector devices.

Hereby samples can be cooled in the same cooling compartment as is used for the fractions without the risk of mixing them.

In one embodiment the cooling compartment comprises at least two holder positions, into which holder positions different types of holders for either fraction collector devices or sample containers can be positioned, whereby the identifying device is arranged to identify if the holder is arranged to hold fraction collector devices.

In one embodiment the cooling compartment comprises a tray comprising the at least two holder positions.

In one embodiment each holder position can be used for either fraction collector device holders or sample container holders and this can be changed between different runs of the chromatography system. Hereby a flexible system is provided where the user himself can decide how to use the space in the cooling compartment for different occasions.

In one embodiment at least the holders that are arranged to hold fraction collector devices are provided with codes that are read by the identifying device.

In one embodiment the cooling compartment comprises at least one port where a sample tube can enter the cooling compartment.

In one embodiment the step of identifying comprises identifying if a holder provided into the cooling compartment is arranged to hold fraction collector devices.

In one embodiment the sample containers can be placed in any one of a number of holder positions provided in the cooling compartment.

In one embodiment the method further comprises to simultaneously fractioning into the fraction collector devices and transferring sample from the sample containers.

DETAILED DESCRIPTION OF EMBODIMENTS OF THE INVENTION

Fraction collector devices have previously been provided in a cooling compartment in chromatography lab systems. Fractions are often collected automatically by a dispenser head into tubes or deep wells. The dispenser head is moved automatically in a specific pattern to collect the fractions in the different tubes or deep wells. The temperature in the cooling compartment can suitably be varied in dependence of what temperature is optimal for the collected fractions.

Figure 1:
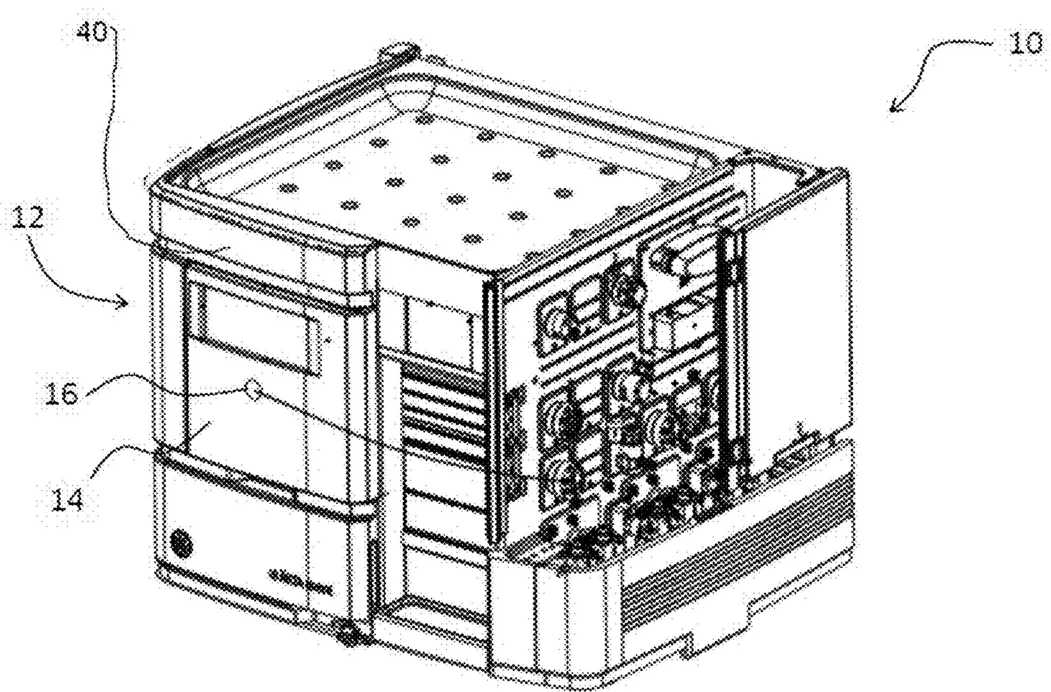
FIG. 1 is a schematic view of a chromatography lab system according to one embodiment of the invention.

FIG. 1 is a schematic view of a chromatography lab system 10 according to one embodiment of the invention. A cooling compartment 12 is provided in the system. A front wall 14 to the cooling compartment can be seen in FIG. 1. The front wall 14 comprises according to the invention at least one port 16 through which a tube for sample can be provided.

The chromatography lab system according to the invention comprises a cooling compartment 12 arranged to hold both fraction collector devices and sample containers. The cooling compartment 12 comprises an identifying device 40 as depicted in FIG. 1, which is arranged to identify the fraction collector devices such that fractions from the chromatography are collected only in the fraction collector devices and not in the sample containers. According to one embodiment, the identifying device 40 can be arranged above and adjacent to the front wall 14.

Figure 2:
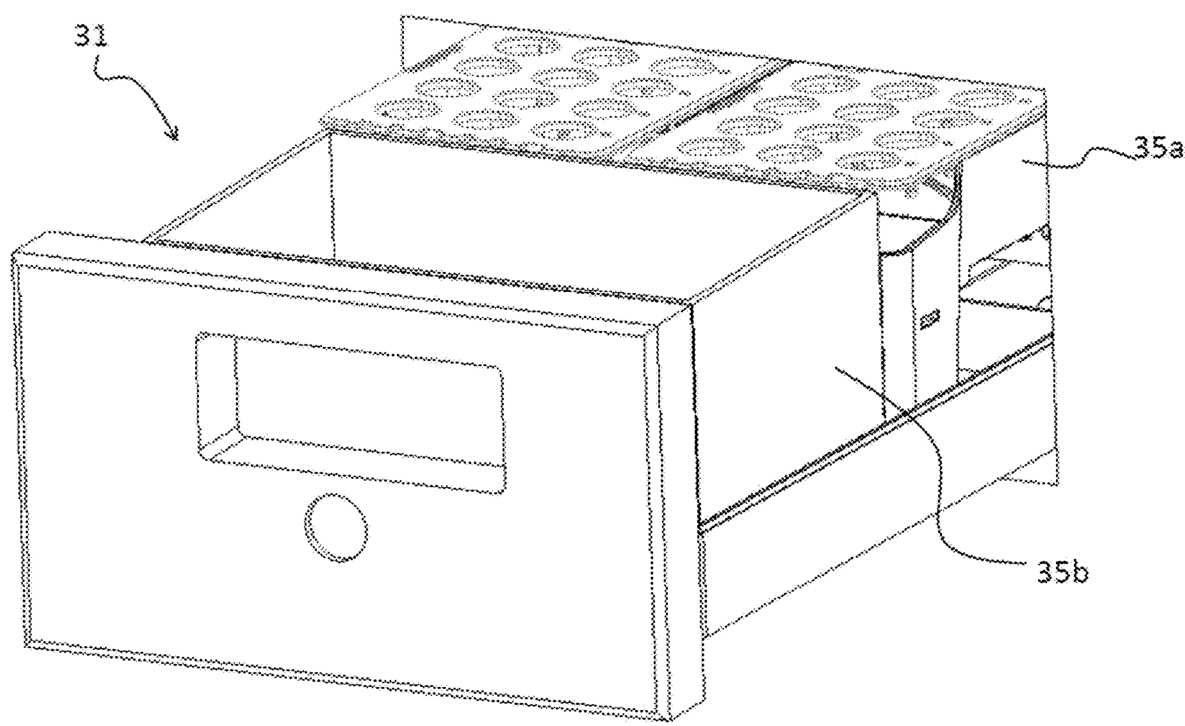
FIG. 2 is a schematic view of a tray comprising holders in a cooling compartment according to one embodiment of the invention.
Figure 3:
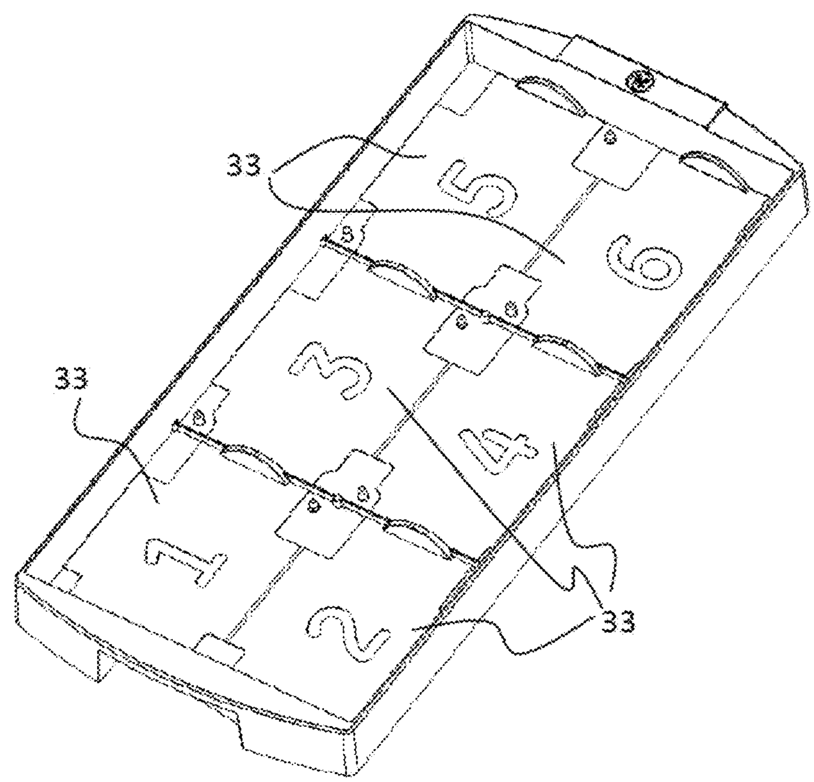
FIG. 3 is a schematic view of the positions in a tray according to one embodiment of the invention.

FIG. 2 is a schematic view of an example tray 31 comprised in a cooling compartment according to one embodiment of the invention. FIG. 3 is a schematic view of the bottom of such a tray as shown in FIG. 2. The tray 31 comprises a number of holder positions 33 into which holders 35 that are designed for holding either fraction collector devices or sample containers are supposed to be positioned. Alternatively no tray is provided in the cooling compartment 12 and instead the holder positions 33 are provided directly on the floor or a bottom part of the cooling compartment. The holders 35 are here called fraction collector device holders 35*a* and sample container holders 35*b*. The number of holder positions 33 is here shown to be six, but any number would be possible, for example 2,3,4,5 or even more than 6. The holders 35 can be designed differently to hold different types of fraction collector devices and sample containers, for example tubes or deep wells of different sizes and numbers and sample containers of different sizes.

The cooling compartment comprises an identifying device 40 as depicted in FIG. 1, which is arranged to identify the fraction collector devices such that fractions are only provided in the fraction collector devices and not in any sample containers. For example codes can be provided to at least the fraction collector device holders 35*a*. These codes should identify these holders as fraction collector device holders and the identifying device 40 provided in the cooling compartment 12 reads the code and determines that fractions can be provided in these holders. If sample container holders 35*b* are not provided with any identification such as code, fractions will not be provided there because these holders cannot be identified by the identifying device 40 as a fraction collector device holder. Another alternative would be to provide also sample container holders 35*b* with a code that is identifying these holders as sample container holders and not as fraction collector device holders. Also in this case the result is that fractions not are provided into these holders.

In one embodiment of the invention the holder positions can be used for any type of holder and this can be changed between each run of the chromatography system. This means that all six positions can be used for fraction collection in one run and in another run any number of the positions can be used for holding samples that need to be cooled.

Sample can be taken from the sample containers through a tube provided through the port 16 in the cooling compartment wall at any time and even at the same time as fractions are collected. The distribution of fractions into the fraction collector devices is usually provided through a dispenser head provided in the cooling compartment.

This cooling compartment that can be used both for cooling fractions and samples provides a more convenient and compact chromatography lab system. External refrigerators or ice baths are avoided. The flexibility in the use of the different holder positions in the tray provides for a flexible system. The user can utilize the limited space in the cooling compartment in an optimal way for each different need in different chromatography runs.

What is claimed is:

1. A chromatography laboratory system comprising:

a cooling compartment comprising:

at least two holder positions configured to receive a plurality of holders, each holder being configured to hold both fraction collector devices for collecting chromatographically separated fractions and sample containers for providing samples for input into the chromatography laboratory system;

wherein, in operation, at least one of the holder positions comprises a holder containing the fraction collector devices, and at least another of the holder positions comprises a holder containing the sample containers; and an identifying device comprising a reader configured to read identifying information assigned to the fraction collector devices, to determine that fractions are supplied to the fraction collection devices, such that said fractions are collected only in the fraction collector devices and not in the sample containers.

2. A chromatography laboratory system according to claim 1, wherein the holder positions are configured to hold different types of fraction collector devices or sample containers, whereby the identifying device is arranged to identify if a respective holder of the plurality of holders is arranged to hold fraction collector devices.

3. A chromatography laboratory system according to claim 2, wherein the cooling compartment comprises a tray comprising the at least two holder positions.

4. A chromatography laboratory system according to claim 3, wherein each of the at least two holder positions is configured to hold either fraction collector device holders or sample container holders and a type of holder is changeable between different runs of the chromatography lab system.

5. A chromatography laboratory system according to claim 4, wherein at least the holders that are arranged to hold fraction collector devices are provided with codes that are readable by the identifying device.

6. A chromatography laboratory system according to claim 5, wherein the cooling compartment comprises at least one port where a sample tube enters the cooling compartment.

7. A method for cooling samples in a chromatography laboratory system comprising a plurality of cooling compartments, comprising the steps of:

placing a sample container in the same cooling compartment as fraction collector devices are stored in, holding, via a plurality of holders received by at least two holder positions, both the fraction collector devices for collecting chromatographically separated fractions and sample containers for providing samples for input into the chromatography laboratory system;

wherein, in operation, at least one of the holder positions comprises a holder containing the fraction collector devices, and at least another of the holder positions comprises a holder containing the sample containers; and reading identifying information assigned to the fraction collector devices via an identifying device comprising a reader, at the same cooling compartment, to determine that fractions can be supplied to the fraction collector devices such that the fractions are collected only in the fraction collector devices and not in the sample containers.

8. The method according to claim 7, further comprising identifying if the holder provided into the cooling compartment is arranged to hold fraction collector devices.

9. The method according to claim 8, wherein the sample containers are placed in any one of a number of holder positions of the at least two holder positions provided in the cooling compartment.

10. The method according to claim 9, further comprising simultaneously collecting fractions into the fraction collector devices and transferring sample from the sample containers.

* * * * *